United States Patent [19]

Viner

[11] Patent Number: 5,981,549

[45] Date of Patent: Nov. 9, 1999

[54] METHOD FOR CONTROLLING OR ALLEVIATING THE SYMPTOMS OF RESPIRATORY DISEASE AND ALLERGIES

[75] Inventor: Norman Viner, Ottawa, Canada

[73] Assignee: Synapse Pharmaceutical International, Ottawa, Canada

[21] Appl. No.: 08/801,802

[22] Filed: Feb. 14, 1997

[51] Int. Cl.$^6$ .......................... A61K 31/44; A61K 31/15
[52] U.S. Cl. .......................... 514/332; 514/357; 514/358; 514/640
[58] Field of Search ...................... 514/640, 332, 514/357, 358

[56] References Cited

U.S. PATENT DOCUMENTS

| | | |
|---|---|---|
| 1,794,292 | 2/1931 | Hollo . |
| 2,816,113 | 12/1957 | Wilson et al. . |
| 2,947,782 | 8/1960 | de Benneville et al. . |
| 2,996,510 | 8/1961 | Green . |
| 3,063,901 | 11/1962 | O'Leary et al. . |
| 3,077,476 | 2/1963 | Hackley, Jr. et al. . |
| 3,852,294 | 12/1974 | Hagedorn . |
| 3,928,594 | 12/1975 | Cook . |
| 3,950,519 | 4/1976 | Mora . |
| 4,002,760 | 1/1977 | Cook . |
| 4,031,218 | 6/1977 | El-Antably . |
| 4,089,959 | 5/1978 | Diamond . |
| 4,120,947 | 10/1978 | Diamond . |
| 4,352,810 | 10/1982 | Benschop et al. . |
| 4,353,922 | 10/1982 | Pfister . |
| 4,675,326 | 6/1987 | Amitai et al. . |
| 4,689,213 | 8/1987 | Golub et al. . |
| 4,816,487 | 3/1989 | Schewe et al. . |
| 4,865,837 | 9/1989 | Harris, III et al. . |
| 4,925,856 | 5/1990 | Harris, III et al. . |
| 4,988,710 | 1/1991 | Olney . |
| 5,096,916 | 3/1992 | Skupin . |
| 5,124,455 | 6/1992 | Lombardo . |
| 5,171,744 | 12/1992 | Cross et al. . |
| 5,206,371 | 4/1993 | Powers et al. . |
| 5,250,286 | 10/1993 | Skupin . |
| 5,292,749 | 3/1994 | Stobie . |
| 5,362,755 | 11/1994 | Barberich et al. . |
| 5,409,934 | 4/1995 | Smith et al. . |
| 5,547,994 | 8/1996 | Barberich et al. . |
| 5,650,444 | 7/1997 | Caggiano et al. . |
| 5,693,659 | 12/1997 | Head et al. . |

FOREIGN PATENT DOCUMENTS 2016920  10/1979  United Kingdom .

OTHER PUBLICATIONS

Simon et al, "Administration of Obidoxime Tablets to Man", Arch. Toxicol, 36:83–88 (1976).

*Primary Examiner*—William R. A. Jarvis

[57] ABSTRACT

Disclosed herein is a method for controlling or alleviating the symptoms of respiratory disease and allergies comprising administering to a mammal suffering from respiratory disease or allergies an effective amount of an acetylcholine esterase reactivator having an oxime moiety optionally in association with an acetylcholine receptor antagonist.

48 Claims, No Drawings

METHOD FOR CONTROLLING OR ALLEVIATING THE SYMPTOMS OF RESPIRATORY DISEASE AND ALLERGIES

BACKGROUND OF THE PRESENT INVENTION

The present invention is directed to a method for controlling and/or alleviating respiratory disease or allergies.

Respiratory diseases are many in number. For instance, bronchoconstriction associated with pulmonary disease is very prevalent and associated with a number of diseases. These diseases include asthma, chronic obstructive pulmonary disease (COPD), and pulmonary hypersensitivity.

Asthma is a term given to a condition whereby a person experiences wheezing and difficulty in breathing due to the constriction of the air passages in the lungs. It has been believed that this state is due to an allergic reaction of some sort and generally non-defined. It is estimated, for example, that 5 million children in the United States alone suffer from the symptoms of asthma. It has also been reported that 500,000 hospital admissions and 5000 deaths each year may be attributable to asthma. COPD affects more than 15 million persons in the United States. COPD symptoms include chronic cough, shortness of breath and difficulty breathing, and predominates in two forms, chronic bronchitis and emphysema.

Additional respiratory diseases such as allergic rhinitis, conjunctivitis, Epiglottis, Laringotrachitis, Urticaria and other allergic and neurodermatitis are often associated with these conditions.

A variety of treatments have been tried to alleviate or control such symptoms. For instance, U.S. Pat. No. 3,950,519 described a process for treatment of allergenically induced asthma by administration of cedar resin which functions as a antiasthmatic agent exhibiting expectorant action to aid in cleansing the lungs of excess mucus. Present asthma treatments involve minimizing contact with allerginic agents as well as use of bronchodilators. However, it is possible that in certain instances the use of a bronchodilator exacerbates the condition rather than provide any long term relief from the symptons due to the gaseous delivery system employed. It has also been proposed to administer methylecgonidine to counteract acetylcholine-induced contraction on tracheal rings as described in U.S. Pat. No. 5,552,407. Bronchoconstriction therapy has also included administration of beta-adrenergic agonists, ipratropium and methylxanthines. Treatment of COPD includes administration of ipratropium (Atrovent), albuterol (Proventil, Ventolin) and theophylline. In extreme cases, lung resection and transplantation are recommended.

Exemplary therapies are disclosed in U.S. Pat. Nos. 1,794,292 (atropine); 4,031,218 (xanthines); 4,089,959 (xanthines); 4,120,947 (xanthines); 4,353,922 (anticholinergic bronchodilators); 4,689,213 (calcium channel blocker); 5,096,916 and 5,250,286 (imidazoline); 5,124,455 (oxime-carbonate and oxime-carbamate); 5,171,744 and 5,292,749 (antimuscarinic bronchodilator); 5,362,755 and 5,547,994 (albuterol); and 5,409,934 (xanthines).

As a complicating factor in the treatment of respiratory disease and allergies, it is believed that factors such as comorbid addictions, stress, psychiatric disorders and environmental factors play a role in determining the extent to which a particular person may be afflicted by the symptoms of respiratory disease and allergies. For example, xenobiotic agents such as pesticides, insecticides, fungicides, oxidants, solvents and other environmental toxins encountered by the person by various means (e.g., drinking water, food contaminantion, smoking, etc.) may contribute to the susceptibility of the person to respiratory disease and allergies as well as the severity of symptoms of such diseases.

A need thus exists to provide a method of treatment of respiratory disease and allergies suffered by mammals and in particular humans which enables the root cause of the respiratory disease and/or allergy to be addressed whereby further occurrences of the disease or allergy are avoided or at the least minimized. It may accordingly be possible, for example, to avoid the need for surgery which may otherwise be required in an attempt to restore acceptable lung function in cases such as extreme COPD.

OBJECTS AND SUMMARY OF THE PRESENT INVENTION

It is accordingly an object of the present invention to provide a method for controlling respiratory disease or allergies or alleviating symptoms of such diseases.

It is a further object of the present invention to provide a method for alleviating symptoms associated with respiratory disease and/or allergies.

It is still further an object of the present invention to provide a method for the treatment of bronchoconstriction associated with pulmonary disease.

It is still further an object of the present invention to provide a method for the treatment of asthma.

In accordance with the present invention, there is accordingly provided a method for controlling or alleviating respiratory disease or allergies comprising administering to a mammal including humans suffering from or subject to respiratory disease or allergies an effective amount of an acetylcholine esterase reactivator optionally in association with an acetylcholine receptor antagonist.

DETAILED DESCRIPTION OF THE PRESENT INVENTION

The present invention involves the administration to a mammal suffering from respiratory disease or allergies an amount of an acetylcholine esterase reactivator effective to alleviate or control such disease or allergies.

The present invention may be used to control and/or alleviate symptoms of respiratory disease or allergies. By way of definition, the present invention is intended to treat diseases of the respiratory tract as well as nasal passages including but not limited to chronic bronchitis and emphysema, asthma, chronic obstructive pulmonary disease (COPD), pulmonary hypersensitivity, allergic rhinitis, Epiglottis, Laringeotrachitis, Urticaria and other allergic and neurodermatitis. Of particular interest for treatment by the present invention is bronchoconstriction, of which asthma is the most prevalent form. It has been found, for example, that by practice of the present invention a relatively immediate alleviation of bronchoconstriction symptoms results. Of particular interest is bronchoconstriction due to chronic obstructive pulmonary disease, such as may be caused by smoking and accompanied by chronic bronchitis or emphysema.

The acetylcholine esterase reactivators which may be employed in the present invention are well known to those skilled in the art and well-described in the literature. Such reactivators found early use as nerve gas and toxic pesticide poisoning antidotes. Exemplary acetylcholine esterase reactivators include but are not limited to those compounds disclosed in U.S. Pat. Nos. 2,816,113; 2,947,782; 2,996,510;

3,063,901; 3,077,476; 3,852,294; 3,928,594; 4,002,760; 4,352,810; 4,675,326; 4,865,837; 4,925,856; 4,988,710; 5,206,371 and U.K. application 2,016,920, each herein incorporated by reference in their entirety.

A preferred class of compounds which may be used as acetylcholine esterase reactivators are oximes. Oximes contain the moiety —CR=NOH and may generally be defined by the formula $(R^1-CR=NOH)^+X^-$ where R is, for example, hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $R^1CR=NOH$ $X^-$ $X^-$ where R is hydrogen, $C_{1-5}$ alkyl or $NH_2$ and $R^1$ is

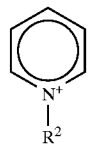

wherein $R^2$ is selected from the group consisting of:

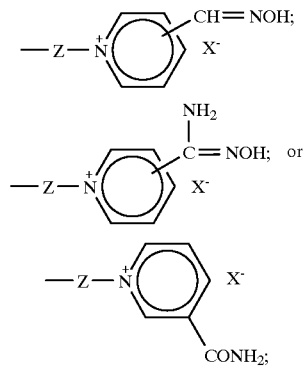

where Z is, for example, a polyalkylene group having from 1 to 6 carbon atoms, optionally including at least one ether linkage, such as —$CH_2CH_2$—, —$CH_2OCH_2$—, —$CH_2CH_2OCH_2CH_2$—, —$CH_2OCH_2CH_2OCH_2$—; or —$(CH_2)$n-phenyl-$(CH_2)$n— where n ranges from 1 to 6 and the phenyl moiety may be substituted by $C_{1-5}$ alkyl, and wherein $X^-$ is a pharmaceutically acceptable anion derived from a salt of an inorganic or organic acid. The above formulae and various substituents are intended to be merely illustrative and not limiting of the identity of the various types of oximes that may be employed with success in the present invention as acetylcholine esterase reactivators. Additional oximes not illustrated above exist which possess the ability to reactivate acetylcholine esterase and which may be employed with advantage in the present invention.

Exemplary acetylcholine esterase reactivators include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis(4-formylpyridinium)halide oximes; 1,1'-(2,5-dimethyl-p-phenylenedimethylene)bis(4-formylpyridinium)halide dioximes; 1,1'-polymethylene bis(3-formylpyridinium) halide dioximes; 1,1'-(p-phenylenedimethylene)bis(3-formylpyridinium)halide dioximes; bis quaternary 4-formylpyriinium halide monooximes; 1,1'trimethylene bis (3-amidooximopyridinium)halides, quaternary pyridine aldoxime (TMB-4); HI-6; diacetyl monoxime; aldoxime-substituted triazolium compounds including 1,4-dimethyl-3-(hydroxyimino)methyl-1,2,4-triazolium chloride, 1-benzyl-3-(hydroxyimino)methyl-4-methyl-1,2,4-triazolium chloride, and 3-(hydroxyimino)methyl-1-methyl-4-(2'-methylsulfonyl-1'-ethyl)-1,2,4-triazolium chloride; and aldoxime-substituted imidazolium derivatives such as 1-([1'-(2'-butynyloxy)methyl]-2-(hydroxyimino)methyl-3-methylimidazolium chloride, 2-(hydroxyimino)methyl-3-methyl-1-[1'-2'-(methylsulfonyl)ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)-1'-ethyl]2-(hydroxyimino)methyl-3-methylimidazolium chloride, 1-[2'-(hydroxyimino)methyl-3'-methyl-1'-imidazolo]-3-(4"-carbamoyl-1"-pyridino)propane dichloride, 1-(3'-bromopropyl-1'-oxy)methyl-2-(hydroxyimino)methyl-3-methylimidazolium chloride, 2-(hydroxyimino)methyl-3-methyl-1-(2'-pyrrdidinium-1'-)ethylimidazolium chloride hydrochloride, 1-(3'-butynyl-1'-thio)methyl-2-(hydroxyimino)methyl-3-methylimidazolium chloride, and 1-[(2'-N-ethyl-N-trifluoromethane sulfonyl)amino-1'-]ethyl-2-hydroxyimino)methyl-3-methylimidazolium chloride.

A preferred class of oximes suitable for use in the present invention may be depicted by the formula:

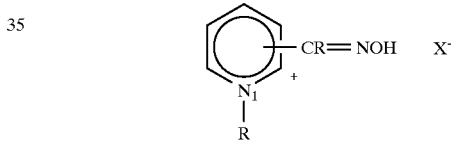

wherein R is hydrogen, $C_{1-5}$ alkyl, or $NH_2$; $R^1$ is $C_{1-5}$ alkyl (particularly methyl or ethyl), and X is an anion portion of the salt $R^1X$. Suitable acid addition salts include the chloride salt, the iodide salt and the methanesulfonate salt.

A specific oxime which is preferred for use in the present invention is 2-PAM chloride which is depicted by the following formula:

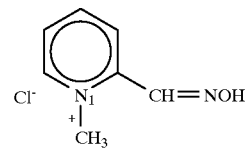

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

In addition to oximes, it has been found that hydrazone, semicarbazone and acyl hydrazone derivatives of 2-formyl-1-substituted pyridinium compounds may be usefully employed as acetylcholine esterase reactivators as described in U.S. Pat. No. 5,206,371, herein incorporated by reference.

The acetylcholine receptor antagonists which may optionally be employed in the present invention are well known to those skilled in the art and well-described in the literature. Exemplary antagonists include but are not limited to (singly or in combination) scopolamine, homatropine, atropine, methscopolamine, methylatropine, ipratropium, methylecgonidine (MEG), mecamylamine, benactyzine, benztropine, trihexyphenidyl, biperiden, procyclidine, benzetimide, dexetimide, iaprophen and pharmaceutically acceptable derivatives thereof. See, for example, U.S. Pat. Nos. 5,011,853 and 5,552,407, herein incorporated by reference in their entirety, which disclose exemplary acetylcholine receptor antagonists. Preferred antagonists are scopolamine and ipratropium. Anticholinergic agents such as ipratropium bromide (Atrovent) are known for use in connection with the treatment of bronchoconstriction. See, Goodman & Gilman's *The Pharmacological Basis of Therapeutics*, 9th edition, 1996.

Acetylcholine esterase reactivators (such as 2-PAM and HI-6) have been used in conjunction with acetylcholine receptor antagonists (such as atropine) to provide in vivo protection against nerve gas agents and other organophosphate poisons. See, for example, U.S. Pat. Nos. 3,063,901; 4,713,391; 4,865,837; and 4,925,856. Atropine (an acetylcholine receptor antagonist) has also been used to treat bronchitis, nasal inflammation, hay fever, etc. as discussed in U.S. Pat. No. 1,794,292. However, an acetylcholine esterase reactivator such as oximes (optionally together with an acetylcholine receptor antagonist or other active agent) has not previously been employed to alleviate the symptoms of respiratory disease or allergies. The amounts of the respective components required to provide the benefits of the present invention are orders of magnitude less than the amounts normally administered to provide protection against nerve gas agents or toxic organophosphate poisoning.

In addition to the acetylcholine esterase reactivator and the acetylcholine receptor antagonist, it is within the scope of the present invention to co-administer additional compounds to assist in achieving the desired result or to provide additional cooperative treatment.

Depending upon the severity of the symptoms, it may be advisable to also administer an anti-asthmatic drug. Exemplary anti-asthmatic drugs include (1) anti-inflammatory drugs such as corticosteroids (Beclomethasone dipropionate, Budesonide, Flunisolide, Triamcinolone acetonide, Prednisone, etc.), Cromolyn, and Nedocromil, and (2) bronchodilators such as $B_2$-selective adrenergic drugs (Albuterol, Bitolterol mesylate, Pirbuterol, Salmeterol and Terbutaline) and Theophylline.

It may also be advantageous to administer a stimulant in association with the cholinesterase reactivator. A preferred stimulant is nicotine. Nicotine may be administered by any appropriate means, including nicotine gum, a nicotine patch, etc. Nicotine administration may occur prior to, during or subsequent to administration of the two compounds. It has been found that the amount of nicotine administered is less than the amount found in a patch or a stick of nicotine gum (e.g., one milligram or so, the amount not being particularly critical).

Other conventional stimulants (such as dopaminergic stimulants) may be administered in lieu of or in addition to nicotine. Such alternative stimulants include but are not limited to mineptine, Amphetamine, Amphetaminil, Bemegride, Benzphetamine, Brucine, Chorphentermine, Clofenciclan, Clortermine, Cocoa, Demanyl Phosphate, Dexoxadrol, Dextroamphetamine Sulfate (Dexedrine), Diethpropion, N-Ethylamphetamine, Ethamivan, Etifelmin, Etryptamine, Fencamfamine, Fenethylline, Fenosolone, Fenfluramine, Flurothyl, Hexacyclonate Sodium, Homocamfin, Mazindol, Megexamide, Methamphetamine, Methylphenidate, Nicotinic agonists, Nikethamide, Pemoline, Pentylenetetrazole, Phenidimetrazine, Phenmetrazine, Phentermine, Picrotoxin, Pipradrol, Prolintane, Pyrovalerone, and Tetrahydrobenzothienopyridines and mixtures thereof.

Xanthines are an additional class of compounds that may be administered in conjunction with the acetylcholine esterase reactivator and one or more of the other optional active ingredients to assist in signal modulation along the dendrite. U.S. Pat. Nos. 4,364,922; 4,980,379; 5,288,721; 5,340,813; 5,354,756; 5,440,041; 5,473,070; 5,567,704; 5,580,873; and 5,580,874 disclose exemplary xanthines which may be used in the present invention, each herein incorporated by reference. Exemplary xanthines include but are not limited to alkylxanthines such as propylxanthine and methylxanthine. Methylxanthines include 1,3,7-trimethylxanthine(caffeine), 3,7-dimethylxanthine (theobromine), 1,3-dimethylxanthine(theophylline), aminophylline, 1,8-dimethyl-3-(2-methyl-1-butyl)xanthine, 1,3-dimethyl-8-(n-propyl)xanthine, 1,4-(4-hydroxypentyl)-3,7-dimethylxanthine, and 7-(3-phenylpropenyl) theophylline. Exemplary propylxanthines include (E)-4-(1, 2,3,6-tetrahydro-1,3-dimethyl-2,6-dioxo-9H-purin-8-yl) cinnamic acid and (E)-4-(1,2,3,6-tetrahydro-2,6-dioxo-1,3-dipropyl-9H-purin-8-yl)cinnamic acid. Prodrug forms of xanthines may also be employed as disclosed in U.S. Pat. No. 4,061,753, herein incorporated by reference. Such forms exhibit enhanced lipid solubility of the compound.

Adenosine antagonists may also be employed in conjunction with one or more of the above. Such compounds reduce the interstitial concentration of adenosine in myocardial tissue. The compounds may either be a competitive inhibitor or a substance that reduces the concentration of adenosine. A variety of compounds may be used as adenosine antagonists including xanthines (such as those discussed above), imidazopyrimidine, pyraxolopyridine, etazolate, pyrazoloquinoline and triazoloquinazoline. Exemplary adenosine antagonists are described in U.S. Pat. Nos. 4,364,922; 4,980, 379; and 5,364,922, each herein incorporated by reference.

As still yet another compound which may be administered in conjunction with one or more of the above is the inhibiting neurotransmitter gamma-aminobutyric acid (GABA) or a precursor thereof such as L-glutamic acid. GABA receptor agonists and other antiepileptics may be employed such as Epival, Baclofen, Sabril, barbiturates, Gabapentin, Lamotrizine and Riluzolo.

It may also be useful to additionally administer an acetylcholine esterase inhibitor such as Phytostigmine, Neostigmine, Demecarium, Pyridostigmine, Velnacrine, Huperzine A, Tacrine, Aricept (Donepezil hydrochloride), Memric, Artane (trihexyphenidyl), Cogentin (benzotropine mesylate), Benedryl (diphenhydramine hydrochloride), Donepezil hydrochloride, etc. It is also within the scope of the present invention to combine administration of the active ingredients with more conventional therapies such as antioxidant treatment, vitamin treatment, heavy metal antagonists such as chelating agents and bile-acid binding resins. The identity of such compounds is well known to those skilled in the art as described in Goodman & Gilman's *The Pharmacological Basis of Therapeutics*, 9th edition, 1996.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope pharmaceutically acceptable salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The compounds of the present invention may be administered by any pharmaceutically acceptable means and in any pharmaceutically acceptable form. For instance, the compounds may be administered orally in the form of pills, tablets, solutions, syrups, lozenges, etc. in which the compound is the sole or co-ingredient as the active agent. The compounds may also be administered parenterally (e.g., intravenously, intramuscularly or subcutaneously) in association with a pharmaceutically acceptable carrier. Topical administration such as by transdermal patch, eyedrops, salves, creams and/or ointments is also acceptable. The active components may also be administered by inhalers or internasally.

Tablets or pills may contain the active ingredient(s) in admixture with conventional pharmaceutically acceptable excipients (i.e., inert diluents). Such tablets or pills may be uncoated or coated by conventional techniques to delay disintegration and absorption in the gastrointestinal tract. More specifically, such tablets or pills may include an enteric coating to ensure disintegration and absorption in the intestine. Such coatings are generally comprised of a cellulose lower fatty acid phthalate such as cellulose acetate phthalate.

In the event that the acetylcholine receptor antagonist is administered together with the acetylcholine esterase reactivator, it is preferred that the acetylcholine receptor antagonist be administered prior to the administration of the acetylcholine esterase reactivator. Such sequential administration can be accomplished, for example, by administering the respective compounds by separate sequential oral or parenteral administration. Alternatively, the respective components can be sequentially administered in the form of a lozenge, tablet or pill which contains the two components in separate layers which will dissolve or disentegrate in sequence. Such sequential administration is not required, however.

The acetylcholine esterase reactivator (and optionally the acetylcholine receptor antagonist) are employed or administered in an amount effective to reduce or prevent symptoms of respiratory disease or allergies suffered by the person, and in particular bronchoconstriction due to pulmonary disease such as asthma. The phrase "reduce or prevent" is intended to refer to any degree of reduction of the symptoms suffered by the person, as well as any degree of prevention of the suffering of such symptoms if administered prior to the onset of such symptoms. That is, the present invention may be used prophylactically as well as to treat presently existing symptoms.

With the above in mind, the various compounds of the present invention may be administered within a wide range of dosage levels while still enabling the benefits of the present invention to be achieved. For example, the acetylcholine receptor antagonist is administered at a dosage level of from 0.001 to 10 mg. The acetylcholine esterase reactivator is administered at a dosage level of from 1 mg to 10 mg. Such dosage levels are based on a standard adult body weight of 70 kg. Additional components such as stimulants are administered in amounts of from 0.1 to 10 mg. The xanthine component, if administered, will generally be administered in an amount of from 25 to 300 mg. Other components that may be co-administered such as anti-asthmatic drugs may be administered in conventional amounts. Such dosage administrations are repeated as required to provide the desired results, with administrations being repeated every 12 to 36 hours depending upon the extent of withdrawal symptoms observed.

The present invention is illustrated by the following examples which are not intended to be limiting of the scope of the invention but merely illustrative of various preferred and specific embodiments.

EXAMPLE 1

A 24 year old female with a 10 year half pack/day smoking history stated that she smoked partially to control her weight. She was given 1 mg nicotine and 0.01 mg of ipratropium followed by 2.5 mg of protopam in sequence on 10 occasions over a period of 2 months by the oral mucosa route of administration. Relief of negative symptoms such as calf muscle cramps, restricted breathing (bronchospasm and bronchial secretions) nasal congestion and fatigue were reported.

EXAMPLE 2

A 39 year old female with mild asthma and allergies was given 5 mg. of Protopam following 0.01 mg. of ipratropium on 3 occasions by an oral mucosa route of administration when feeling "chesty and nasal". Following each sequential trial a relief of symptoms was reported which lasted for 12 to 36 hours.

EXAMPLE 3

A 35 year old male competitive fitness trainer with mild asthma and allergies and chronic muscle strain described as a tightness about his neck, shoulders and upper back had consulted unsuccessfully with professionals of other disciplines for relief. The patient was given 5 mg. of Protopam sl following 1 mg of nicotine and 0.01 mg of ipratropium by the oral mucosa route on 2 different occasions. Following each administration the patient reported profound relief of his symptoms lasting approximately 4 days.

From the above description, one of ordinary skill in the art can readily ascertain the essential characteristics of the present invention. Without departing from the scope of the invention, various changes and/or modifications can be made which are still within the scope and range of equivalence of the attached claims.

What is claimed is:

1. A method for preventing or alleviating symptoms of respiratory disease and allergies in a mammal comprising administering to a mammal suffering from respiratory disease or allergies an amount effective to prevent or control such symptoms of an active agent comprising an acetylcholine esterase reactivator or pro drug derivative thereof, with the proviso that said acetylcholine estersase reactivator includes an oxime moiety and with the further proviso that said acetylcholine esterase reactivator is not an aryl oxime.

2. The method of claim 1 wherein said oxime moiety is —CR=NOH where R is hydrogen, $C_{1-5}$ alkyl or $NH_2$.

3. The method of claim 1 wherein said acetylcholine esterase reactivator is administered in a pharmaceutically acceptable carrier.

4. The method of claim 1 wherein said reactivator is selected from the group consisting of monoquaternary oximes, bisquaternary oximes, and triquaternary oximes.

5. The method of claim 1 wherein said acetylcholine esterase reactivator is an oxime salt.

6. The method of claim 5 wherein said salt is an acid addition salt selected from the group consisting of a chloride, iodide and methanesulfonate salt.

7. The method of claim 6 wherein said acetylcholine esterase reactivator is a chloride salt of an oxime.

8. The method of claim 7 wherein said oxime is 2-pyridine aldoxime methochloride (2-PAM Cl).

9. The method of claim 1 wherein said acetylcholine esterase reactivator is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), pro-drug compounds thereof and pharmaceutically acceptable salts thereof.

10. The method of claim 1 wherein said mammal suffers from the symptoms of bronchoconstriction associated with pulmonary disease.

11. The method of claim 10 wherein said bronchoconstriction is associated with asthma.

12. The method of claim 10 wherein said bronchoconstriction associated with pulmonary disease is caused by chronic obstructive pulmonary disease.

13. The method of claim 10 wherein said bronchoconstriction associated with pulmonary disease is caused by emphysema.

14. The method of claim 1 wherein said respiratory disease is selected from the group consisting of allergic rhinitis, Epiglottis, Laringotrachitis, Urticaria and allergic neurodermatitis.

15. A method for preventing or alleviating symptoms of respiratory disease and allergies in a mammal comprising administering to a mammal suffering from respiratory disease or allergies an amount effective to prevent or control such symptoms of an active agent selected from the group consisting of:

(1) a compound defined by the formula $(R^1-CR=NOH)^+X^-$ where R is hydrogen, $C_{1-5}$ alkyl or $NH_2$, $R^1$ is $C_{1-5}$ alkyl and $X^{31}$ is a pharmaceutically acceptable anion derived from a salt of an inorganic acid or a salt of an organic acid;

(2) a compound defined by the formula $(R^1-CR=NOH)^+X^{31}$ where R is hydrogen, $C_{1-5}$ alkyl or $NH_2$ and $R^1$ is a 5 or 6 membered heterocyclic moiety having from 1 to 3 nitrogen atoms in the heterocyclic ring and $X^-$ is a pharmaceutically acceptable anion derived from a salt of an inorganic acid or a salt of an organic acid;

(3) a compound defined by the formula $R^1-CR=NOH^+ X^-$ where R is hydrogen, $C_{1-5}$ alkyl or $NH_2$ and $R^1$ is

wherein $R^2$ is selected from the group consisting of:

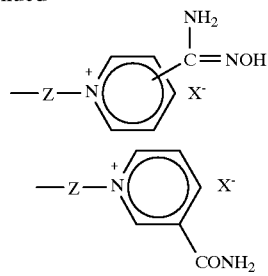

where Z is a polyalkylene group having from 1 to 6 carbon atoms, optionally including at least one ether linkage, or $-(CH_2)n$-phenyl-$(CH_2)n-$ where n ranges from 1 to 6 and the phenyl moiety may be optionally substituted by $C_{1-5}$ alkyl, and wherein $X^-$ is a pharmaceutically acceptable anion derived from a salt of an inorganic acid or a salt of an organic acid; and (4) prodrug derivatives of the compounds of (1)–(3) above.

16. The method of claim 15 wherein said active agent is administered in a pharmaceutically acceptable carrier.

17. The method of claim 15 wherein said salt is an acid addition salt selected from the group consisting of a chloride, iodide and methanesulfonate salt.

18. The method of claim 17 wherein said active agent is a chloride salt.

19. The method of claim 15 wherein said active agent is 2-pyridine aldoxime methochloride (2-PAM Cl).

20. The method of claim 15 wherein said active agent is selected from the group consisting of 1-methyl-pyridinium-2-aldoxime (2-PAM),2,3-butanedione-2-oxime (DAM), pyruvaldehyde aldoxime (MINA), bis quaternary pyridine aldoxime (TMD-4), HI-6, obidoxime, prodrug compounds thereof and pharmaceutically acceptable salts thereof.

21. The method of claim 15 wherein said mammal suffers from the symptoms of bronchoconstriction associated with pulmonary disease.

22. The method of claim 15 wherein said mammal suffers from the symptoms of bronchoconstriction associated with asthma.

23. The method of claim 21 wherein said bronchoconstriction associated with pulmonary disease is caused by chronic obstructive pulmonary disease.

24. The method of claim 21 wherein said bronchoconstriction associated with pulmonary disease is caused by emphysema.

25. The method of claim 15 wherein said mammal suffers from respiratory disease selected from the group consisting of allergic rhinitis, Epiglottis, Laringotrachitis, Urticaria and allergic neurodermatitis.

26. The method of claim 15 wherein said active agent is defined by the formula $R^1-CR=NOH^+X^-$ where R is hydrogen, $C_{1-5}$ alkyl or $NH_2$ and $R^1$ is

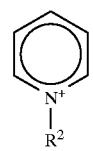

wherein R² is selected from the group consisting of:

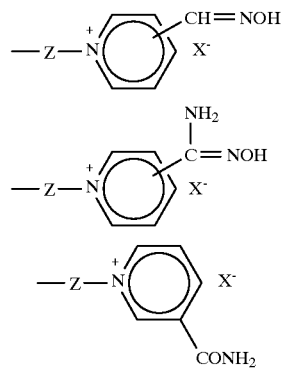

where Z is a polyalkylene group having from 1 to 6 carbon atoms, optionally including at least one ether linkage, or —(CH₂)n-phenyl-(CH₂)n— where n ranges from 1 to 6 and the phenyl moiety may be optionally substituted by $C_{1-5}$ alkyl, and wherein X⁻ is a pharmaceutically acceptable anion derived from a salt of an inorganic acid or a salt of an organic acid.

27. The method of claim 26 wherein said mammal suffers from the symptoms of bronchoconstriction associated with pulmonary disease.

28. The method of claim 26 wherein said mammal suffers from the symptoms of bronchoconstriction associated with asthma.

29. The method of claim 27 wherein said bronchoconstriction associated with pulmonary disease is caused by chronic obstructive pulmonary disease.

30. The method of claim 27 wherein said bronchoconstriction associated with pulmonary disease is caused by emphysema.

31. The method of claim 26 wherein said mammal suffers from respiratory disease selected from the group consisting of allergic rhinitis, Epiglottis, Laringotrachitis, Urticaria and allergic neurodermatitis.

32. The method of claim 15 wherein said active agent is defined by the formula $(R^1—CR=NOH)^+X^-$ where R is hydrogen, $C_{1-5}$ alkyl or NH₂, R¹ is $C_{1-5}$ alkyl and X⁻ is a pharmaceutically acceptable anion derived from a salt of an inorganic acid or a salt of an organic acid.

33. The method of claim 32 wherein said mammal suffers from the symptoms of bronchoconstriction associated with pulmonary disease.

34. The method of claim 32 wherein said mammal suffers from the symptoms of bronchoconstriction associated with asthma.

35. The method of claim 33 wherein said bronchoconstriction associated with pulmonary disease is caused by chronic obstructive pulmonary disease.

36. The method of claim 33 wherein said bronchoconstriction associated with pulmonary disease is caused by emphysema.

37. The method of claim 32 wherein said mammal suffers from respiratory disease selected from the group consisting of allergic rhinitis, Epiglottis, Laringotrachitis, Urticaria and allergic neurodermatitis.

38. The method of claim 15 wherein said active agent is defined by the formula $(R^1—CR=NOH)^+X^-$ where R is hydrogen, $C_{1-5}$ alkyl or NH₂ and R¹ is a 5 or 6 membered heterocyclic moiety having from 1 to 3 nitrogen atoms in the heterocyclic ring and $X^{31}$ is a pharmaceutically acceptable anion derived from a salt of an inorganic acid or a salt of an organic acid.

39. The method of claim 38 wherein said mammal suffers from the symptoms of bronchoconstriction associated with pulmonary disease.

40. The method of claim 38 wherein said mammal suffers from the symptoms of bronchoconstriction associated with asthma.

41. The method of claim 40 wherein said bronchoconstriction associated with pulmonary disease is caused by chronic obstructive pulmonary disease.

42. The method of claim 41 wherein said bronchoconstriction associated with pulmonary disease is caused by emphysema.

43. The method of claim 38 wherein said mammal suffers from respiratory disease selected from the group consisting of allergic rhinitis, Epiglottis, Laringotrachitis, Urticaria and allergic neurodermatitis.

44. The method of claim 1 wherein said mammal suffers from the symptoms of bronchoconstriction associated with pulmonary disease.

45. The method of claim 44 wherein said bronchoconstriction is associated with asthma.

46. The method of claim 44 wherein said bronchoconstriction associated with pulmonary disease is caused by chronic obstructive pulmonary disease.

47. The method of claim 44 wherein said bronchoconstriction associated with pulmonary disease is caused by emphysema.

48. The method of claim 1 wherein said respiratory disease is selected from the group consisting of allergic rhinitis, Epiglottis, Laringotrachitis, Urticaria and allergic and neurodermatitis.

* * * * *